United States Patent [19]

Hunter et al.

[11] 3,932,532

[45] Jan. 13, 1976

[54] ETHERS OF POLYGLYCEROL

[75] Inventors: Robert H. Hunter, Mendenhall, Pa.; John David, deceased Zech, late of Wilmington, Del., by Mary Barth Zech, executrix

[73] Assignee: ICI United States Inc., Wilmington, Del.

[22] Filed: June 1, 1973

[21] Appl. No.: 365,861

[52] U.S. Cl. ............ 260/615 R; 252/351; 252/396; 260/615 B; 424/337; 424/342; 427/180; 428/224
[51] Int. Cl.² ................... C07C 43/04; C07C 41/02
[58] Field of Search ..................... 260/615 R, 615 B

[56] References Cited
UNITED STATES PATENTS

| | | | |
|---|---|---|---|
| 2,258,892 | 10/1941 | Harris | 260/615 R |
| 2,552,529 | 5/1951 | De Groote | 260/615 B X |
| 2,626,918 | 1/1953 | De Groote | 260/484 D |
| 2,679,520 | 5/1954 | De Groote | 260/615 B X |
| 2,733,272 | 1/1956 | Horsley et al. | 260/615 B |
| 2,831,034 | 4/1958 | Pruitt et al. | 260/615 B |
| 2,932,670 | 4/1960 | Blake | 260/615 B |
| 3,427,248 | 2/1969 | Lomberti et al. | 260/615 B X |
| 3,742,069 | 6/1973 | Hunter | 260/615 R |

OTHER PUBLICATIONS

Shibata et al., Bull. Japan Petrol. Inst., 7 pp. 25–30. (1965).

*Primary Examiner*—Howard T. Mars

[57] ABSTRACT

Ethers of polyglycerols and an improved method of preparing said ethers are disclosed. The ethers are prepared by reacting a purified polyglycerol with an alpha olefin epoxide in the presence of an alkali metal alkoxide catalyst.

14 Claims, No Drawings

ETHERS OF POLYGLYCEROL

BACKGROUND OF THE INVENTION

1. Field of the Invention

The present invention relates generally to alkyl ethers of polyglycerols and to a method of preparing said ethers. More particularly, the invention relates to alkyl ethers prepared by reacting a purified polyglycerol with an alpha olefin epoxide of the general formula

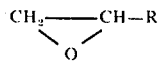

wherein R is an alkyl group containing from 8 to 20 carbon atoms, said reaction being conducted in the presence of an alkali metal alkoxide catalyst.

2. Description of the Prior Art

A variety of surfactants have been reported in the literature. As is now well known, the utility of "ester-type" surfactants — i.e., those containing an

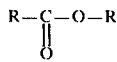

linkage — is limited by virtue of the fact that these surfactants hydrolyze when exposed to either acidic or alkaline environments. One solution to this problem is the use of "ether-type" surfactants — i.e., those containing an R — O — R linkage. Although these materials do not hydrolyze as readily as the ester-type surfactants, ethers of polyhydric materials, such as polyglycerols, have previously been difficult to prepare or resulted in only non-homogeneous or dark colored products having only limited utility.

Ethers of polyhydroxy materials, including di- and polyglycerols, have been described in the literature. See, in this regard, U.S. Pat. Nos. 2,258,892 and 2,302,121, both of which are issued to Harris. However, if the ethers are prepared from polyglycerols containing 3 or more glycerol units, there results only non-homogeneous or highly colored products of very limited utility.

It would, therefore, be desirable to produce homogeneous, light colored, ether derivatives of polyglycerols.

SUMMARY OF THE INVENTION

In accordance with the present invention, homogeneous, light colored, alkyl ethers of polyglycerols are prepared by reacting a purified polyglycerol, as will be defined hereinafter, with an alpha olefin epoxide of the general formula

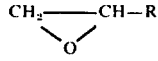

wherein R is $C_8-C_{20}$ alkyl, in the presence of an alkali metal alkoxide catalyst.

DESCRIPTION OF THE PREFERRED EMBODIMENTS

In accordance with the present invention, alkyl ethers of polyglycerols are prepared by reacting, in the presence of an alkali metal alkoxide catalyst, a purified polyglycerol and an alpha olefin epoxide. Each of these materials is described in detail below.

Polyglycerol

As used herein, the term polyglycerol refers to those materials which contain an average of at least 3 glycerol units.

The polyglycerols useful in the present invention are prepared by reacting glycerol at a high temperature in the presence of an alkaline catalyst such as sodium hydroxide. During the course of the reaction, water is split off resulting in the formation of the desired polyglycerol. However, as the polymerization reaction proceeds, generally at temperatures as high as about 250° or 260°C., some organic acids are produced as by-products. These acids react with the alkaline catalyst to form salts thereby lowering the pH of the reaction mixture. Thus, an aqueous solution of the reaction mixture which initially had a pH of at least about 12 will become neutral or only slightly alkaline by the time the reaction reaches the decaglycerol stage and will then continue to become progressively more acidic as the polymerization proceeds beyond that point. As a result, the crude polyglycerol contains about 1 mol of the salts of these organic acids for each mol of alkaline catalyst employed in the reaction.

In preparing the ethers of the present invention, it has been found to be essential to employ a purified polyglycerol in the reaction. As used herein, the term purified polyglycerol refers to a material which has been rendered substantially free of any metals, organic acids, or salts of said metals and acids.

Any method known in the art for removing impurities from polyglycerols may be employed in the present invention. However, preferred results have been achieved with a polyglycerol which has been purified in accordance with the following procedure. This procedure is described in detail in U.S. patent application Ser. No. 52,704, filed July 6, 1970, now U.S. Pat. No. 3,742,069 by Robert H. Hunter entitled "Purification of Polyglycerols" and comprises:

1. Preparing a slurry of an aqueous solution of a crude polyglycerol and an inert, finely divided solid filtering aid at a pH of from 10 to 12. The solid filtering aids which may be employed include any porous, finely divided material which is chemically inert in the reaction mixture. Typical materials which may be employed include, for example, finely ground calcium carbonate, silicas, alumina, diatomaceous earth, and Fullers earth.
2. Separating the solid and liquid phases of the slurry by any conventional means such as filtration or centrifugation.
3. Passing the liquid phase through an anionic exchange resin to remove essentially all of the organic anion constituents present.
4. Passing the liquid phase through a cationic exchange resin to remove the metal ions present in the material.

If desired, the purified polyglycerol may be subjected to a treatment with activated carbon to reduce the color of said material prior to use in the preparation of the ethers of the present invention.

Although any of the above-mentioned purified polyglycerols may be utilized, preferred results have been achieved with materials containing from about 8 to about 12 glycerol units — i.e., octaglycerol to dodecaglycerol. Especially preferred results have been achieved with a material containing 10 glycerol units — i.e., decaglycerol.

Alpha Olefin Epoxide

The alpha olefin epoxide which is reacted with the purified polyglycerol to prepare the alkyl ethers of the present invention is selected from compounds of the general formula

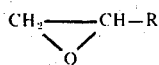

wherein R is an alkyl group containing from about 8 to about 20 carbon atoms. It has been found that, if epoxides with alkyl substituents having less than about 8 carbon atoms are employed, the resulting products are too hydrophilic to be useful as surfactants. Also, if epoxides with alkyl substituents having more than about 20 carbon atoms are employed, the resulting products are too hydrophobic to be useful.

The alpha olefin epoxides may be utilized either as individual compounds or as mixtures of 2 or more of the aboveidentified materials. Representative epoxides which may be employed include, for example, NEDOX 1518, a mixture of epoxides of the above formula wherein R is a straight-chain alkyl group containing from 13 to 16 carbon atoms; and NEDOX 1114, a mixture of epoxides wherein R is a straight-chain alkyl group containing from 9 to 12 carbon atoms, both of which are available from ADM Chemicals, a division of Ashland Oil and Refining Company, Minneapolis, Minnesota. Other epoxides which may be employed include 1,2-epoxy decane; 1,2-epoxy dodecane; 1,2-epoxy octadecane and the like.

To produce the homogeneous, light colored reaction products of the present invention, the amount of epoxide employed should be equal to at least 1 mol per mol of polyglycerol. Additional epoxide may be employed depending upon the desired properties of the resulting product. In general, as the amount of any given epoxide is increased, the product becomes more hydrophobic — i.e., more lipophilic.

Catalyst

In reacting the purified polyglycerol with the alpha olefin epoxide to produce the homogeneous, light colored ethers of the present invention, it has been found to be essential to employ, as a catalyst for the reaction, an alkali metal alkoxide. This catalyst may be prepared by reacting an alkali metal with a hydroxyl-containing compound, such as methanol, ethanol, ethylene glycol and the like, and adding the resulting alkali metal alkoxide to the reaction mixture containing the purified polyglycerol and the alpha olefin epoxide. Alternatively, the catalyst may be prepared in situ by adding the alkali metal directly to the reaction mixture resulting in the formation of an alkoxide of the polyglycerol.

The amount of catalyst employed is preferably equal to from about 0.1% to about 2.0% by weight based on the weight of polyglycerol in the reaction mixture. If less than about 0.1% catalyst is employed, the reaction is too slow to be practical as a commercial operation. Also, if more than about 2.0% catalyst is used, no further increase in reaction rate is noted and there is, therefore, no reason for including the additional catalyst. Preferred results have been achieved with an amount of catalyst equal to from about 0.5% to about 1.0% by weight based on the weight of polyglycerol in the reaction mixture.

The etherification reaction of the present invention is carried out under anhydrous conditions and it is, therefore, necessary to dry the polyglycerol employed. This may be done, for example, by vacuum stripping the material to a temperature of about 125°C. at a pressure of about 0.35 mm. mercury.

After the polyglycerol has been dried, the alkali metal alkoxide catalyst, or alkali metal if the catalyst is to be formed in situ, is added. If an alkali metal alkoxide is utilized, the catalyst is preferably added dissolved in a suitable solvent such as methanol, ethanol, and the like.

Following the addition of the catalyst, the mixture is again stripped to remove any added solvent and the alpha olefin epoxide is added. This material is preferably added gradually over of period of time.

The resulting reaction mixture is then heated, preferably under a nitrogen atmosphere, to an elevated temperature to increase the rate of the reaction. The actual temperature employed is not narrowly critical to the present invention and only affects the reaction rate. However, it has been found that preferred results are achieved if the reaction is carried out at temperatures in the range of from about 130° to about 170°C. It is especially preferred to carry out the reaction at a temperature of about 150°C.

The reaction mixture is maintained at this elevated temperature until a sample removed therefrom remains homogeneous when cooled to room temperature. As mentioned above, one advantage of the process of the present invention is the production of homogeneous products. As used herein, the term homogeneous refers to a product which exists as a single phase at room temperature. When heated at a temperature within the preferred range mentioned above, the reaction is generally completed in a period of time of from about 2 to about 4 hours.

After the product has become homogeneous, the reaction mixture is cooled, while maintaining the nitrogen atmosphere, and the product recovered. If desired, the cooling step may be interrupted when the temperature of the reaction mixture is about 90°C. and the product bleached by adding about 1% by weight, based on the weight of product, of a 35% hydrogen peroxide solution. Another advantage of the products of the present invention is that they are readily bleachable, to a colorless or light colored product. In addition to the hydrogen peroxide treatment mentioned above, any other bleaching treatment known in the art may be employed. By comparison, ethers of polyglycerol prepared other than in accordance with the present invention are either non-homogeneous or dark colored and incapable of being bleached.

The resulting products may be either mono ethers or higher ethers depending upon the amount of alpha olefin epoxide added to the reaction mixture. As used herein, the term mono ether refers to an ether prepared by reacting 1 mol of epoxide with 1 mol of polyglycerol.

The alkyl ethers of polyglycerol prepared in accordance with the present invention are useful as surfactants having improved hydrolytic stability under both acidic and alkaline conditions making them especially useful in cosmetic applications, as textile lubricants and as corrosion inhibitors. Additionally, these ethers have more free hydroxyl groups than the previously available ether-type surfactants making them useful in applications where other ethers cannot be employed.

In order to describe the present invention so that it may be clearly understood, the following examples are set forth. These examples are set forth primarily for the purpose of illustration and any enumeration of detail contained therein should not be interpreted as a limitation on the concept of the present invention.

EXAMPLE 1

Into a three-necked flask equipped with stirrer and thermometer, there was added 500 grams of a purified polyglycerol containing an average of 10 glycerol units having an acid number of 3, a hydroxyl number of 898, a percent sulfated ash of 0.2, and a percent water of 1.5. Water was then removed from this material by vacuum stripping to a temperature of 125°C. at a pressure of 0.35 mm. Hg. ABS. There was then added 20 cc. of a 25% by weight solution of sodium methylate in methanol and the resulting mixture was vacuum stripped, under the same conditions as described above, to remove the methanol. There was then added 376 grams of NEDOX 1518, an alpha olefin epoxide of the following formula

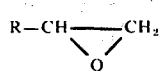

wherein R is a straight-chain alkyl group containing from 13 to 16 carbon atoms.

The resulting reaction mixture was heated, under a nitrogen atmosphere, to a temperature of 150°C. and held at this temperature for a period of 4 hours at the end of which time the reaction mixture became homogeneous. The mixture was then cooled to 90°C. and the product bleached by adding 10 cc. of 35% hydrogen peroxide solution.

The product, which was the hydroxy alkyl ether of decaglycerol, was a soft, light yellow wax weighing 881 grams. The product had an acid number of 0.5, a saponification number of 3.2, a hydroxyl number of 506, a percent sulfated ash of 0.75, and a percent water of 1.0.

EXAMPLE 2

Into a three-necked flask equipped with stirrer and thermometer, there was added 500 grams of the purified polyglycerol described in Example 1 and the material was vacuum stripped to remove water, also as described in Example 1. There was then added 10 cc. of 25% sodium methylate in methanol and the mixture was again vacuum stripped to remove the methanol. There was then added 280 grams of NEDOX 1114, an alpha olefin epoxide of the following formula

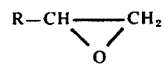

wherein R is a straight-chain alkyl group containing from 9 to 12 carbon atoms.

After reacting, cooling, and bleaching as described in Example 1, there was isolated 773 grams of the hydroxy alkyl ether which was a light yellow, viscous liquid having an acid number of 0.9, a saponification number of 5.0, a hydroxyl number of 585, a percent sulfated ash of 0.5, and a percent water of 1.3.

EXAMPLE 3

The procedure of Example 1 was repeated except that the amount of NEDOX 1518 was reduced by 50% — i.e., to 188 grams — to prepare the monoether rather than the diether prepared in Example 1. Employing the same reaction sequence and procedure as described for Example 1, there was isolated a light yellow wax. This product had an acid number of 0, a saponification number of 1.1, a hydroxyl number of 630, a percent sulfated ash of 0.95, and a percent water of 1.0.

EXAMPLE 4

The procedure described in Example 2 was repeated except that the amount of NEDOX 1114 employed was reduced by 50% — i.e., to 140 grams. After reaction, cooling, and bleaching as described in Example 2, there was isolated the monoether as a light yellow, viscous liquid. This product had an acid number of 0.4, a saponification number of 3.6, a hydroxyl number of 700, a percent sulfate ash of 1.0, and a percent water of 1.2.

EXAMPLE 5

Into a three-necked flask equipped with a stirrer and thermometer, there is added 240 grams (1 mol) of a purified polyglycerol containing an average of 3 glycerol units. The material is stripped to remove any water and there is then added 4.8 grams (2% by weight based on the weight of polyglycerol) of sodium ethylate dissolved in 25 cc. of ethanol. The resulting mixture is again stripped at the end of which time there is added 156 grams (1 mol) of 1,2-epoxy decane.

The resulting reaction mixture is heated to 130°C. until a sample removed from the reaction mixture remains homogeneous at room temperature. At this time, the reaction mixture is cooled and the product, identified as the monoether of triglycerol, recovered.

EXAMPLE 6

The procedure of Example 5 is repeated except that the amount of 1,2-epoxy decane is increased to 212 grams (2 mols) to prepare the diether of triglycerol.

Similarly, the procedure of Example 5 is again repeated utilizing 368 grams (3 mols) of 1,2-epoxy decane to prepare the triether of triglycerol.

EXAMPLE 7

Into a three-necked flask equipped with a stirrer and thermometer, there is added 388 grams (1 mol) of a purified polyglycerol containing an average of 5 glycerol units. The material is stripped to remove any water and there is then added 0.388 grams (0.1% by weight based on the weight of polyglycerol) of sodium metal. The mixture is then heated under vacuum at a temperature of from about 100° to about 120°C. until the sodium metal has dissolved in the polyglycerol forming the sodium alkoxide of the polyglycerol. There is then gradually added 1,340 grams (5 mols) of 1,2-epoxy octadecane.

The resulting reaction mixture is heated to about 130°C. until a sample removed from the reaction mixture is homogeneous at room temperature. At this time, the reaction mixture is cooled and the product, identified as the pentaether of pentaglycerol, is recovered.

What is claimed is:

1. A method of preparing an alkyl ether of polyglycerol, said method comprising reacting (1) a purified polyglycerol containing from 8 to 12 glycerol units which polyglycerol has been purified by a process comprising
a. polymerizing glycerol in the presence of an alkaline catalyst to obtain a crude polyglycerol;
b. preparing an aqueous slurry, at a pH of from 10 to 12, of said crude polyglycerol and an inert, finely divided solid filtering aid;
c. separating a solid phase and a liquid phase of said slurry;
d. passing said liquid phase through an anionic exchange resin; and
e. subsequently passing said liquid phase through a cationic exchange resin and (2) an alpha olefin epoxide of the general formula

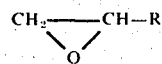

wherein R is an alkyl group containing from 8 to 20 carbon atoms, provided that
i. the amount of epoxide employed is equal to at least 1 mol per mol of purified polyglycerol,
ii. the reaction is carried out under anhydrous conditions and at a temperature of 130° – 170°C, and
iii. the reaction is carried out in the presence of an alkali metal alkoxide catalyst in an amount equal to from 0.1% to 2.0% by weight based on the weight of polyglycerol employed.

2. A method, as claimed in claim 1, wherein the alpha olefin epoxide is a mixture of alpha olefin epoxides.

3. A method, as claimed in claim 2, wherein the alkyl portion of said olefin epoxides contains from about 9 to about 12 carbon atoms.

4. A method, as claimed in claim 2, wherein the alkyl portion of said olefin epoxides contains from about 13 to about 16 carbon atoms.

5. A method, as claimed in claim 1, wherein the polyglycerol contains about 10 glycerol units.

6. A method, as claimed in claim 1, wherein the alkali metal alkoxide catalyst is sodium methoxide.

7. A method, as claimed in claim 1, wherein the alkali metal alkoxide catalyst is formed in situ by adding an alkali metal to the polyglycerol.

8. A method, as claimed in claim 1, wherein the amount of alkali metal alkoxide is equal to from about 0.5% to about 1.0% by weight based on the weight of polyglycerol.

9. A method, as claimed in claim 1, wherein the polyglycerol and the epoxide are reacted at a temperature of about 150°C.

10. A homogeneous alkyl ether of polyglycerol comprising the reaction product of (1) a purified polyglycerol containing from 8 to 12 glycerol units which polyglycerol has been purified by a process comprising
a. polymerizing glycerol in the presence of an alkaline catalyst to obtain a crude polyglycerol;
b. preparing an aqueous slurry, at a pH of from 10 to 12, of said crude polyglycerol and an inert, finely divided solid filtering aid;
c. separating a solid phase and a liquid phase of said slurry;
d. passing said liquid phase through an anionic exchange resin; and
e. subsequently passing said liquid phase through a cationic exchange resin and (2) an alpha olefin epoxide of the general formula

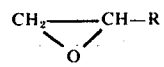

wherein R is an alkyl group containing from 8 to 20 carbon atoms, provided that
i. the amount of epoxide employed is equal to at least 1 mol per mol of purified polyglycerol,
ii. the reaction is carried out under anhydrous conditions and at a temperature of 130° – 170°C, and
iii. the reaction is carried out in the presence of an alkali metal alkoxide catalyst in an amount equal to from 0.1% to 2.0% by weight based on the weight of polyglycerol employed.

11. An ether, as claimed in claim 10, wherein the polyglycerol contains about 10 glycerol units.

12. An ether, as claimed in claim 10, wherein the alpha olefin epoxide is a mixture of alpha olefin epoxides.

13. An ether, as claimed in claim 12, wherein the alkyl portion of said olefin epoxides contains from about 9 to about 12 carbon atoms.

14. An ether, as claimed in claim 12, wherein the alkyl portion of said olefin epoxides contains from about 13 to about 15 carbon atoms.

* * * * *